United States Patent [19]

Schmidt

[11] Patent Number: Plant 7,222

[45] Date of Patent: Apr. 24, 1990

[54] MAGNIFICENT MAGENTA MAPLE

[75] Inventor: Melvin L. Schmidt, P.O. Box 246, Wathena, Kans. 66090

[73] Assignees: Melvin L. Schmidt; Kathleen A. Schmidt, both of Wathena, Kans.

[21] Appl. No.: 241,054

[22] Filed: Sep. 6, 1988

[51] Int. Cl.[5] ..... A01H 5/00

[52] U.S. Cl. ..... Plt./51

[58] Field of Search ..... Plt. 51

[56] References Cited

U.S. PATENT DOCUMENTS

P.P. 5,053 5/1983 Pellett ..... Plt. 51

*Primary Examiner*—James R. Feyrer

[57] ABSTRACT

This invention is of a new and unique variety of *Acer rubrum,* the red maple or swamp maple, which I have now named 'Magnificent Magenta.' I discovered the parent tree, a member of *Acer rubrum,* growing at the end of a cultivated boundary line row of trees along the eastern property line of a residence in Wathena, Kans. The tree is monecious, has leaves of widely varied size and shape, a rounded crown, and an unusual and attractive fall coloration which is long lasting before leaf fall.

6 Drawing Sheets

BACKGROUND AND SUMMARY OF THE VARIETY

Brilliant, unique magenta fall leaf color. The primary attribute of this tree which commanded my attention was its true magenta fall leaf color which is a brilliant, eye-catching red-violet. My observation that the parent tree had superior fall leaf color was confirmed by experts at the Kansas State University arboretum who compared leaves from the parent with those of various cultivars including 'Red Sunset,' October Glory,' and standard trees of the *Acer rubrum* species. Trees of the species have fall leaf color ranging from yellow to dull red to bright red, but none are known to exhibit the striking magenta of this cultivar. Having a magenta fall leaf color enables this tree to fill another niche in the list of trees with purplish shades of fall leaf color which have become increasingly popular in recent years.

Onset, length and durability of fall leaf color. This variety normally assumes its fall leaf color in late September here in the heart of America. It usually lasts about six weeks which provides color into early November.Observation in recent years demonstrates that the leaf color can survive one or more hard frosts which terminate the leaf color of other trees thus providing color when other trees are already losing their leaves.

Specimens three or more years old planted in the ground and adequately watered and fertilized will provide rapid growth of at least 1½ to two feet per year which is a desirable rate of growth for a red maple.

Dense, symmetrical crown. Another desirable characteristic of this variety is that it has a well-shaped, compact, symmetrical oval crown as good as the red maple "Northwood", U.S. Plant Pat. No. 5,053.

My continued observation of the specimens propagated asexually from the parent in 1977 has convinced me that this desirable combination of brilliant, persistent, magenta fall leaf color and well-shaped, compact, symmetrical oval crown is unique and distinguishes thiscultivar from the species and all other varieties thereof known to me.

ASEXUAL REPRODUCTION

I rooted stem cuttings from the parent tree under continuous mist during the hours of sunlight in the summer of 1977 and have subsequently transplanted the ones which rooted into increasingly larger containers as they grew.

BRIEF DESCRIPTION OF THE DRAWING

Sheet One of the drawing shows the tree, in side view, with its distinctive magenta fall coloration;

Sheet Two depicts the same tree, from nearly the same angle, during the summer;

Sheet Three is a close-up color photo which depicts the flowers of the variety;

Sheet Four is a close-up showing the fruiting habit and samara coloration;

Sheet Five is a hand rendered drawing which depicts several of the varied leaf shapes which are formed by the tree; and, Sheet Six is a color photographic showing of the tree in bloom stage before leaf break, showing floral coloration and the branching habit of the new maple tree.

SUMMARY OF CHARACTERISTICS OF THE CULTIVAR

All color references hereinafter are to: *Color: Universal Language and Dictionary of Names,* by Kenneth L. Kelly and Deane B. Judd, National Bureau of Standards (U.S.), Publ. 440, (Dec. 1976) and *ISCC-NBS Color-Name Charts Illustrated with Centroid Colors,* by Kenneth L. Kelly, National Bureau of Standards (U.S.), Supplement to NBS Circular 553. Color terms of ordinary dictionary usage are also occasionally used.

PROPAGATION

I propagated the specimen trees by rooting cuttings from the parent tree under continuous mist during the hours of daylight in Wathena, Kans., in 1977. I have grown the resulting genetically identical specimens from that time primarily in Wathena, Kans. Since the specimens were reproduced by rooted cuttings rather than by grafting scions on rootstocks from other members of the *Acer rubrum* specie, there is no possibility of a rootstock affecting the growth and characteristics of the specimens. Resulting specimens are identical to the parent in all distinguishing characteristics proving the plant to be stable.

TREE

Form — This variety has a compact, well-shaped, symmetrical oval crown which is much more desirable than the somewhat loosely shaped crown typical of the species as a whole. This compact crown results from the fact that the main branches form an angle of normally no more thanfifteen degrees (15°) with each other and are more numerous than usual. The angles formed by the main branches with the main trunk progresses from ten degrees (10°) for the innermost branches to forty degrees (40°) for the outside branches. The smallness of the angle between the branches themselves causes the crown to be compact with a well-rounded symmetrical oval shape, rather than the loosely-formed, less symmetrical crown more typical of the species as a whole.

An additional benefit of the desirable crown characteristics of this cultivar is that specimens propagated asexually from this tree would be less expensive to grow to marketable size in a nursery because they would require less labor for pruning to a shape which would appeal to the average retail buyer.

Trunk — The bark of the trunk of the young specimens is smooth and a light gray in color, ISCC-NBS #10 pinkgray. The bark of the older, mature parent tree is rough and a darker gray. The original tree has a height of only approximately forty-five (45′) feet at maturity which is considerably less than the maximum height of seventy-five to one hundred feet (75′–100′) usually cited as normal for the species. If this diminished height is not due to some limiting effect of the particular soil or climate here, that characteristic would make this variety far more desirable for use as a street tree than the normally larger members of the species. Unfortunately there is no way to determine this until the asexually propagated specimens reach maturity which is a good many years away.

Branches — The parent tree has no main, central leader above the main trunk. Plural, very upright stems branch out into several main near-vertical branches about nine feet (9′) above the ground. The branches of the parent tree have only a small angle between each other as noted above, but have shown no clear sign of weakness. The bark of the branches and trunk of the young specimens is a smooth, light gray, ISCC-NBS #10, pink gray. The trunk and branches of the parent tree are rougher and darker gray in color, somewhere in between ISCC-NBS #264, light gray, and #265, medium gray. The spread of the tree is equal to approximately ninety percent of the height of the tree.

Foliage — The upper side of the stems of the leaves are the same color as the buds and blossoms, a bright red, ISCC-NBS #13, deep red. The under sides of the stems shade from this color to a light green, ISCC-NBS #119, light yellow green. The petioles vary from 4 cm to 10 cm in length depending on the size of the leaf.

The leaves are palmate with three to seven, but normally five or seven lobes. The leaf shapes are widely variable in both shape and size; basal leaf portions may have two or four lobes of disparate shapes. The outermostthree lobes are more uniformly steeple-shaped in plan. The margins of the leaves are serrated with two to three serrations per centimeter. Serrations are not uniform. This maple has leaves of varied sizes: typically a range of smaller leaves approximately 6–7 cm wide×6–7 cm long to larger leaves of approximately 9–10 cm wide×8 cm long are produced.

The color of the upper side of the lamina or leaf blade in summer is a desirable #137, dark yellowish green. The underside of the leaves is much lighter green, ISCC-NBS #122, gray yellow green. The upper side of the leaf is glabrous. The underside of the leaf is glabrous except at the point where the veins join the petiole at the bottom of the lamina where there is a small amount of pubescence between the veins.

The overall fall leaf color of ISCC-NBS #260, very dark purple red, in the color photographs is as close tothe actual color seen by the human eye as I could achieve with a 35 mm camera. However, the true fall color as perceived upon viewing it is a more vivid, true magenta which is closer to a color midway between color ISCC-NBS #256, deep purplish red, and ISCC-NBS #257, very deep purplish red. This is a result of the fact that this maple has a wide range of sizes of leaves, with leaves of varied size and exposure leaving a different, pleasing range of fall color. The smaller leaves are initially a bright red (color #11, vivid red) which eventually deepens to color #260 very dark purplish red) shortly before leaf fall. The larger leaves have a margin of color ISCC-NBS #257, very deep purplish red, with a center of color ISCC-NBS #260 very dark purplish red. Very shortly before leaf fall, both sizes of leaves entirely turn to color ISCC-NBS #260, very dark purlish red. The overall effect is an attractive striking magenta.

From the initial appearance of fall leaf color until shortly before leaf fall, the rays of light reflected from these two different colors of leaves are combined in the eye to be perceived as a brilliant magenta between color ISCC-NBS #256, deep purplish red, and ISCC-NBS #257, very deep purplish red, not altogether captured by the camera. On a bright fall day the color of the leaves is so intense that it literally appears to shimmer in the crisp air.

With the increase in popularity of purplish leaf color in shrubs and trees in recent years, this variety of *Acer rubrum* should be a valuable addition to the varieties already commercially available.

Flower Buds and Flowers — The buds and blossoms are bright red, ISCC-NBS #13, deep red. The buds are approximately three centimeters (3 cm) in diameter and are obovate in shape. In Wathena, Kans. the flowering usually begins in late March to early April depending, on yearly climatic conditions. The size of the flowers varies from 1½ cm to 5 cm for the total distance from the end of the pedicel to the anthers. This variety is monoecious because it has both male and female flowers.

Seeds — The disamaras are typical of the species. The wings of the immature samaras are the same bright red as the flowers. ISCC-NBS #13, deep red, while the seed itself is a light green, ISCC-NBS #116, brilliant yellow green. The ripe samaras are a light brown, ISCC-NBS #76, light yellow brown; the seed itself is ISCC-NBS #56, deep brown; and, the tip of the seed is ISCC-NBS #59, dark brown. The samaras vary from 2 cm to 2½ in length and from ½ cm to 1 cm in width at the widest part of the wing of the samara. A medium quantity of seed is borne. The seed matures toward the end of April in most years and dispersion is normally complete by early May.

General Characteristics — Compared to other members of *Acer rubrum,* this new variety exhibits a unique and desirable magenta fall leaf color, a well-shaped, compact, symmetrical oval crown, adequately rapid growth, and possibly a mature size sufficiently smaller than other members of the species to make its ultimate size superior for street planting.

I claim:

1. A new and unique variety of red maple, *Acer rubrum,* as described and illustrated, being particularly distinguished as to novelty by a combination of the shape of the tree which exhibits a desirable well-shaped, compact, symmetrical oval crown in contrast to the species which is often loosely shaped and much less compact, and a brillant, true magenta fall leaf color quite unlike that of other members of the species and any patented variety; the vivid magenta exhibited during most of the fall leaf color period dictates the name I have chosen for this tree: 'Magnificent Magenta Maple.'

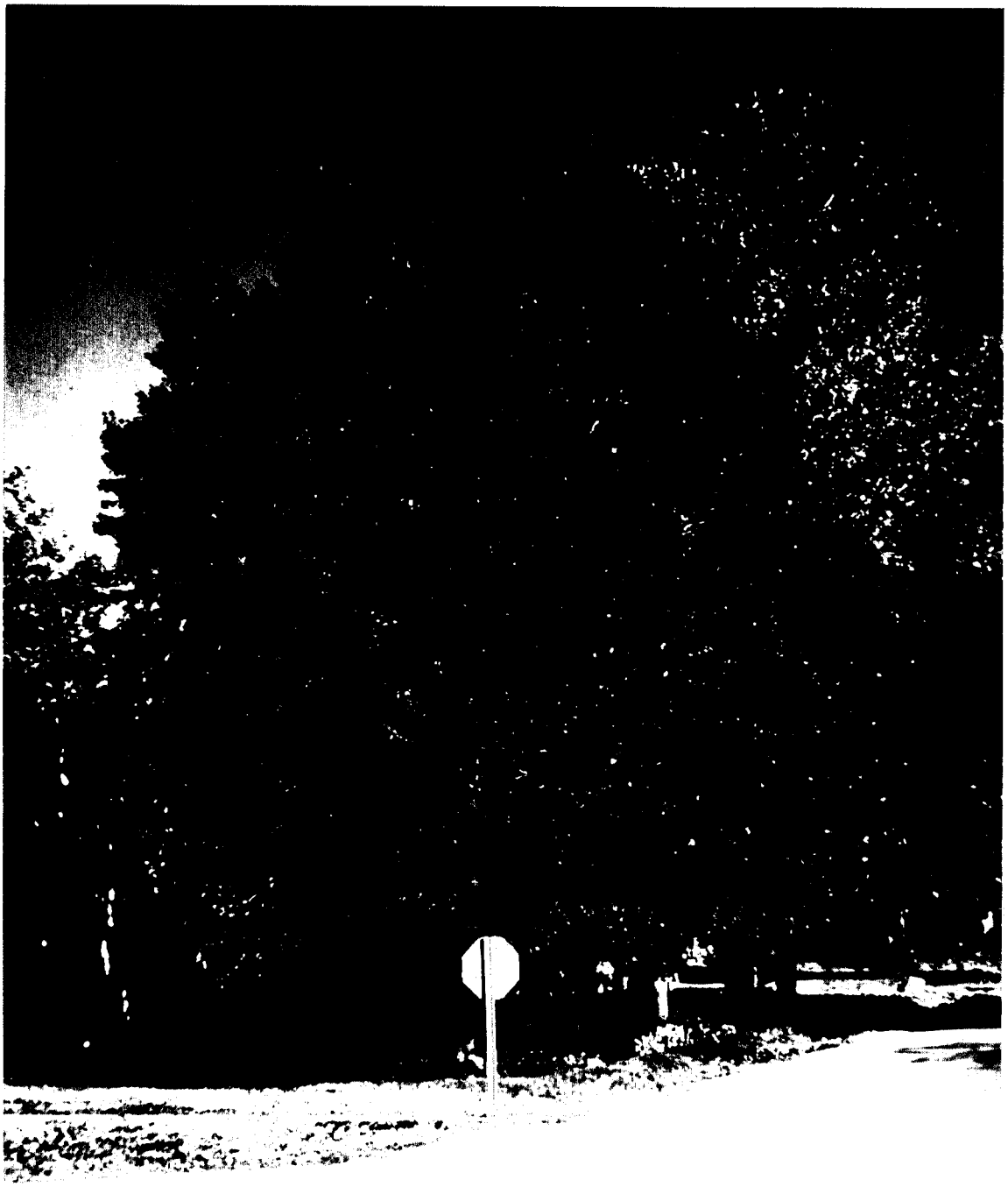

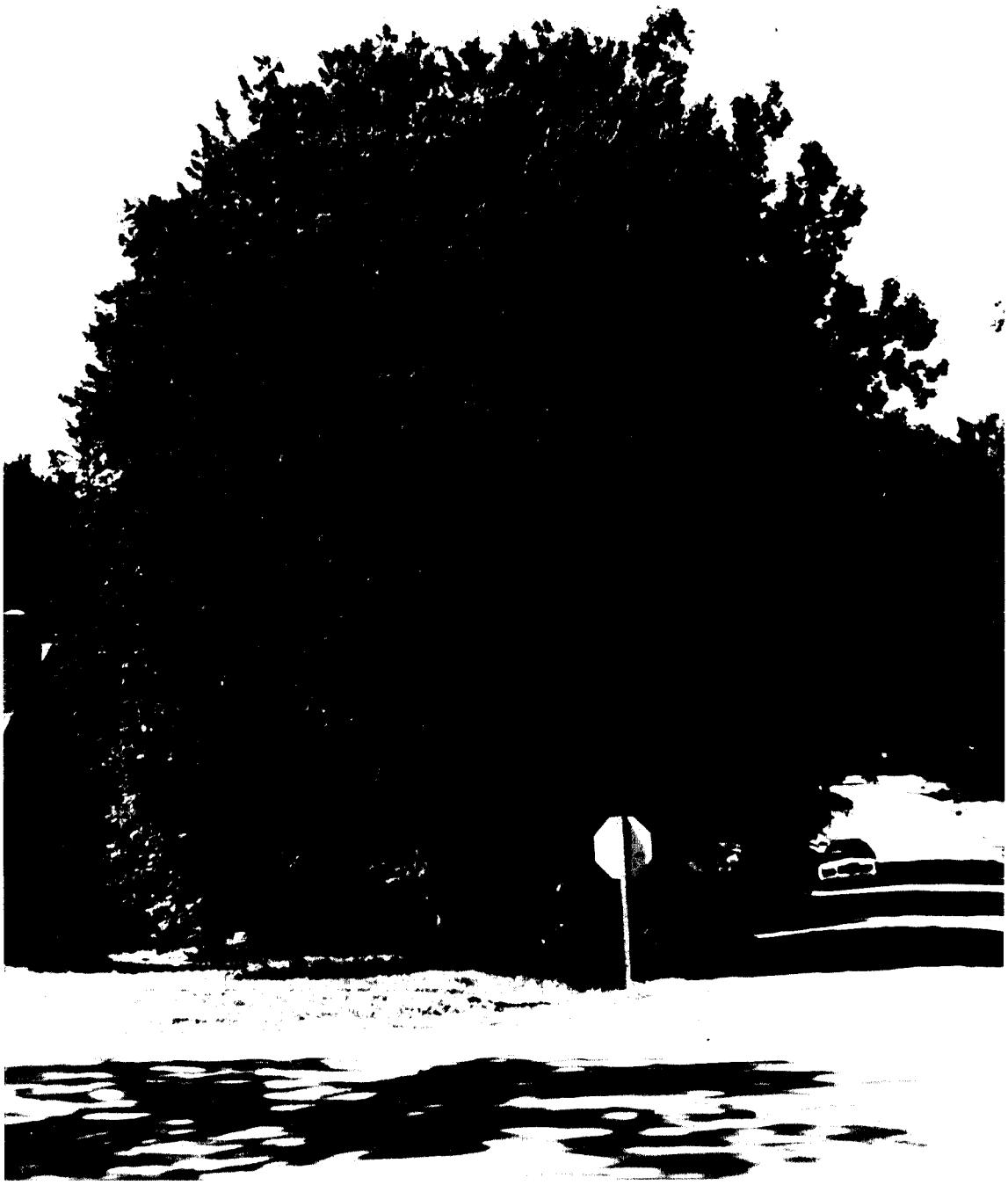

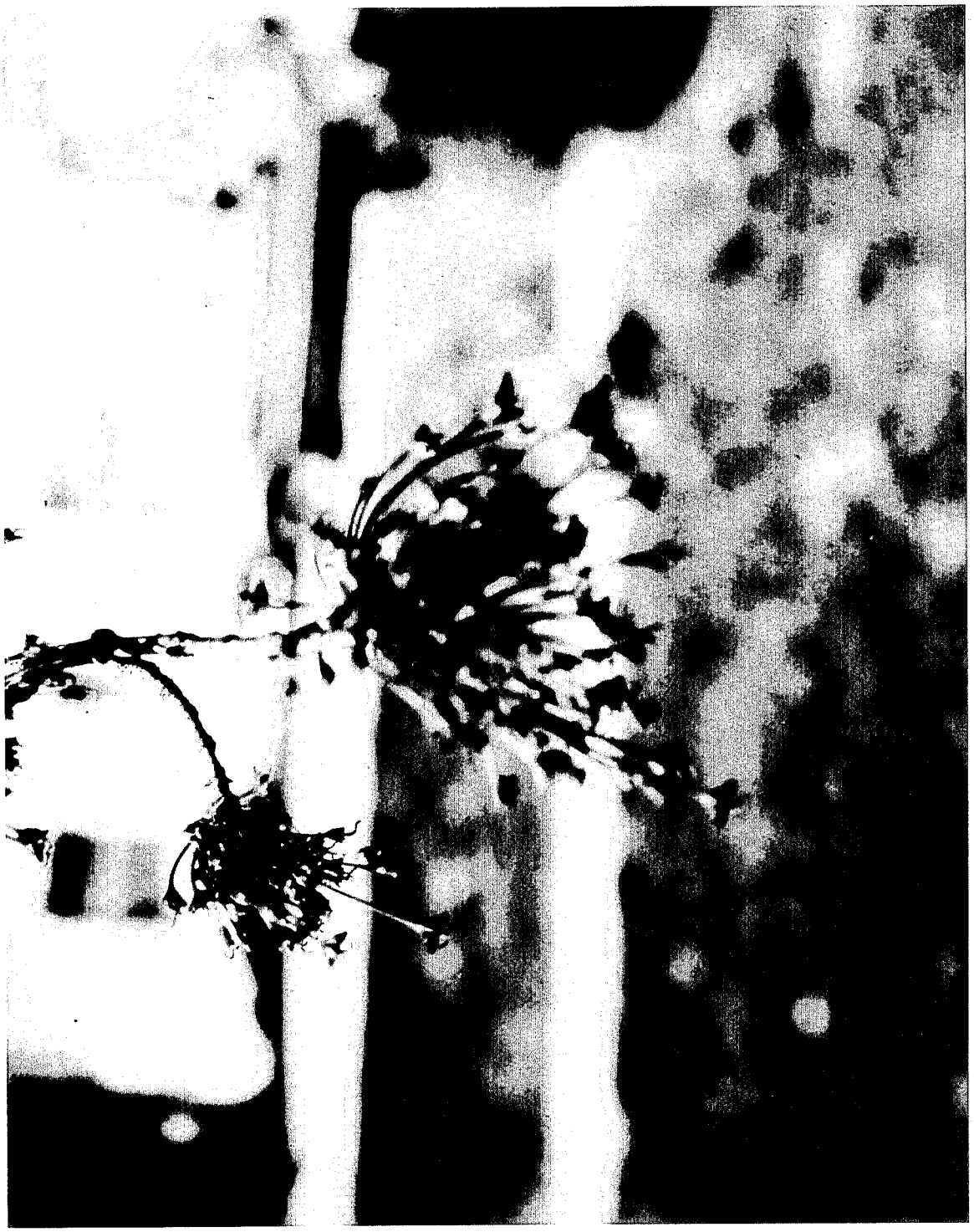

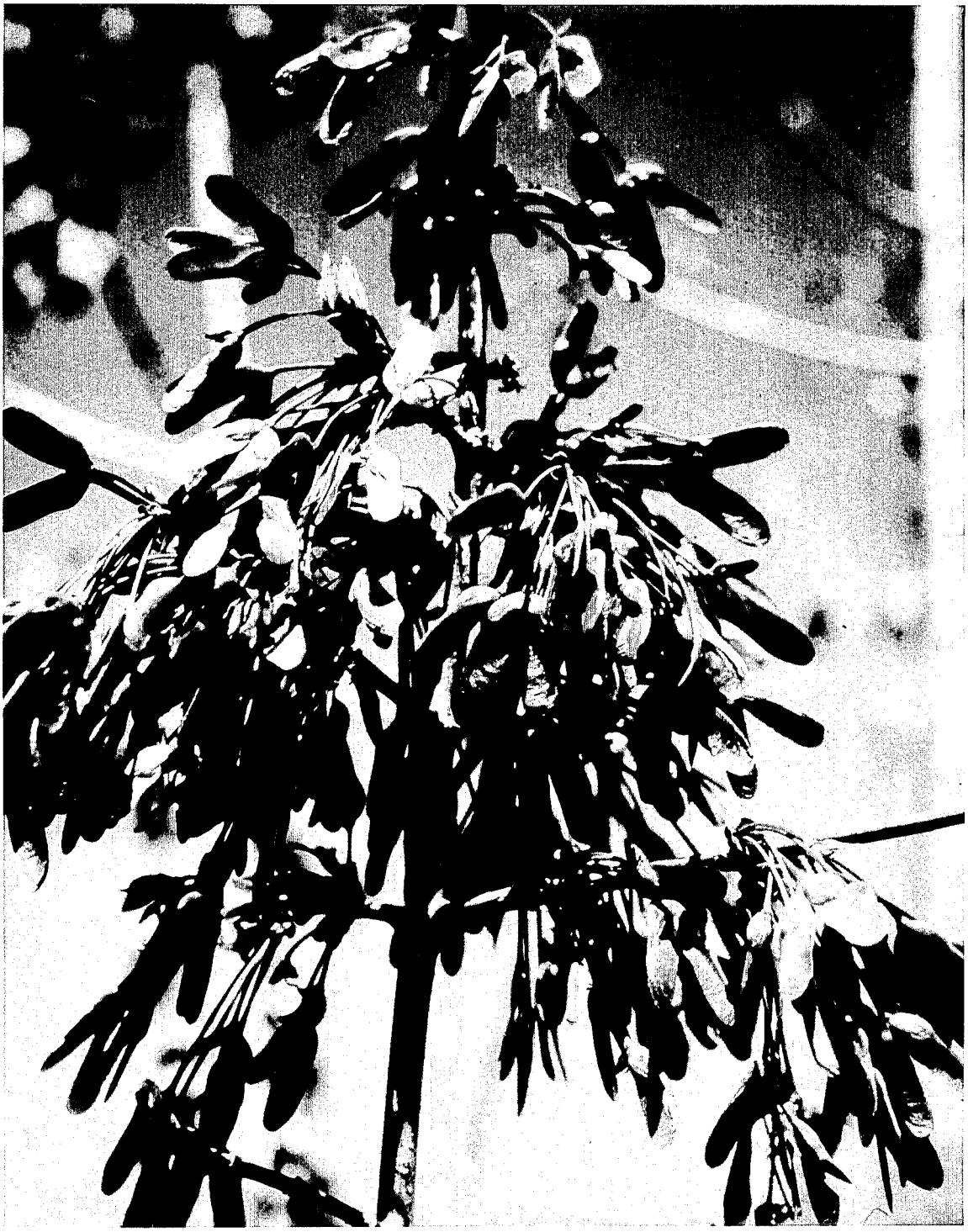

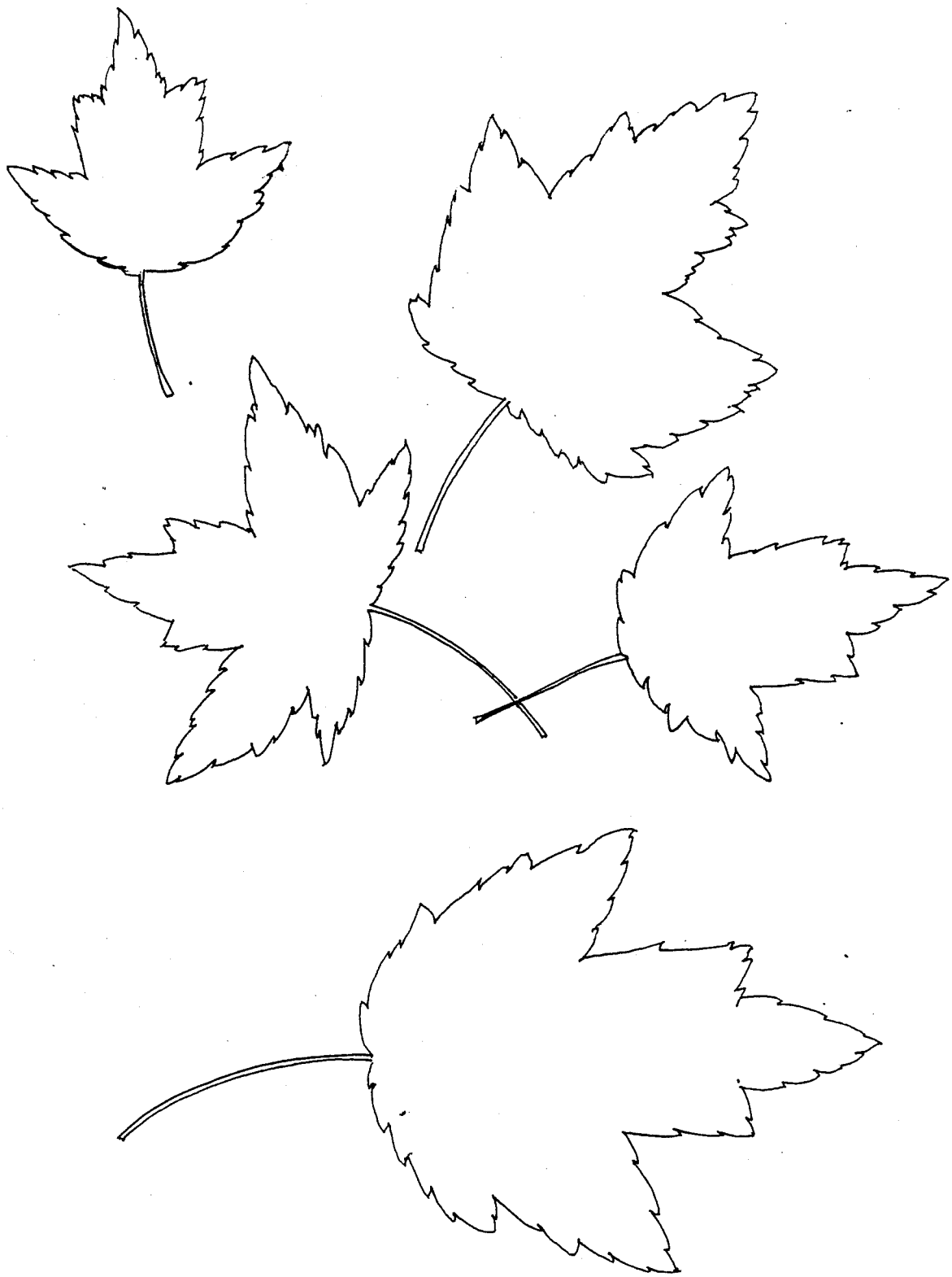

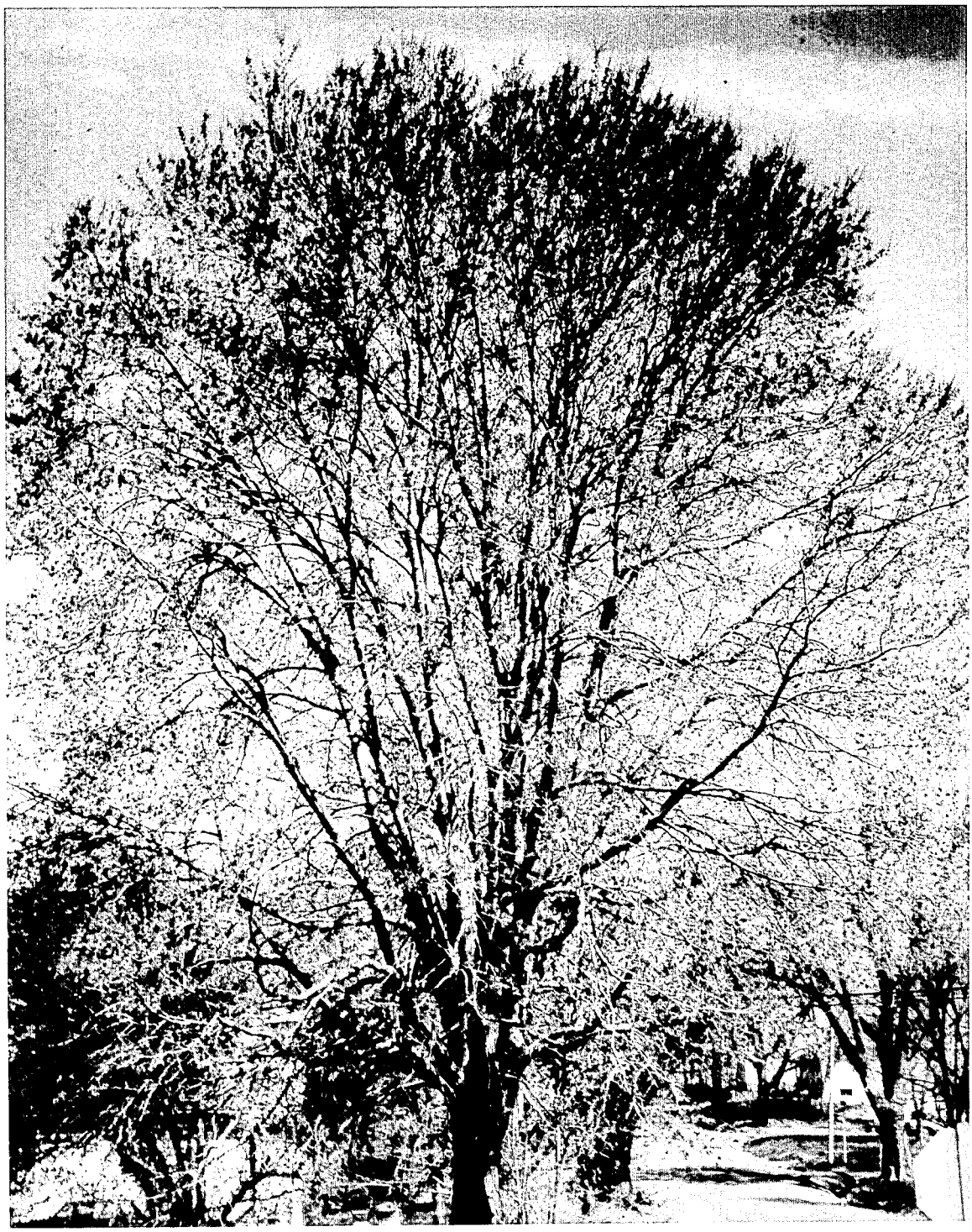

* * * * *